United States Patent [19]

Preti et al.

[11] 4,385,125

[45] May 24, 1983

[54] METHOD DETECTING OVULATION BY MONITORING DODECANOL CONCENTRATION IN SALIVA

[75] Inventors: George Preti, Philadelphia; James G. Kostelc, Glenside, both of Pa.; Joseph Tonzetich, Vancouver, Canada; George R. Huggins, Wallingford, Pa.

[73] Assignee: Monell Chemical Senses Center, Philadelphia, Pa.

[21] Appl. No.: 206,949

[22] Filed: Nov. 14, 1980

[51] Int. Cl.$^3$ .................... G01N 33/48; G01N 33/50
[52] U.S. Cl. ........................ 436/65; 436/131
[58] Field of Search ................... 23/230 B; 436/65

[56] References Cited

U.S. PATENT DOCUMENTS

| | | | | |
|---|---|---|---|---|
| 3,813,222 | 5/1974 | Vietes | ................ | 23/230 B |
| 3,986,494 | 10/1976 | Preti et al. | ................ | 128/2 R |
| 4,010,738 | 3/1977 | Preti et al. | ................ | 128/2 R |
| 4,119,089 | 10/1978 | Preti et al. | ................ | 128/2 R |

OTHER PUBLICATIONS

Chemical Abstracts, 90:69617g and Index page 2164cs (1979).

"Analysis of Human Vaginal Secretions by Gas Chromatography Mass Spectrometry", by George Preti et al.; Israel Journal of Chemistry; vol. 17, 1978; pp. 215-222.

Fenaroli's Handbook of Flavor Ingredients, vol. 2 (2nd Ed.) Ed., Trans., and Revised by Furia and Bellanca, p. 19.

Merck Index (9th Ed. 1976) p. 41.

Doty, R., "Procedure for Combining Mestrual Cycle Data", Journal of Clinical Endocrinology & Metabolism, vol. 48, No. 6, Jun. 1979 pp. 912-918.

Moss, C. W. and S. B. Dees, 1976 "Cellular Fatty Acids and Metabolic Products of Pseudomonas Species Obtained From Clinical Specimens"; *Journal of Clinical Microbiology* 4: 492-502.

Wade, T. J. and R. J. Mandel, 1974, "New Gas Chromatographic Characterization Procedure: Preliminary Studies On Some Pseudomonas Species", *Applied Microbiology* 27: 303-311 Feb. 1974.

Charles D. Cox and J. Parker, "Use of 2-aminoacetophenone Production in Identification of *Pseudomonas aeruginosa*", Apr. 1979 9: 479-484, *Journal of Clinical Microbiology*.

"Development of Specific Tests for Rapid Detection of E. Coli and Species of Proteus in Urine" by N. J. Hayward, et al., *Journal of Clinical Microbiology* Sep., 1977 6: 195-201.

Volatile Compounds Produced in Sterile Fish (*Sebastes malanops*) by *Psuedomonas putrefaciens, Pseudomonas fluorescens,* and an Achromobacter Species", by Miller et al., Applied Microbiology, 26: 18-21 Jul. 1973.

"High Resolution Gas Chromatographic Profiles of Volatile Organic Compounds Produced by Microorganisms at Refrigerated Temperatures" by Lee et al. Applied and Environmental Microbiology No. 1 37: 85-90 Jan. 1979.

"Epidemiology of *Pseudomonas aeruginosa* Infections: Determination by Pyocin Typing" by Brunn et al. (1976) *Journal of Microbiology, 3:264-271.*

"Pseudomonas Carrier Rates of Patients with Cystic Fibrosis and of Members of their Families" by Laraya-Cuasay et al., *Journal of Pediatrics,* 89:23-26 (1980).

"Gas Chromatography Application in Microbiology and Medicine" by Mitruka (1979), John Wiley & Sons, New York, Chapter 13, pp. 352-374.

"Further Studies on the Differentiation of *Clostridium sordelli* from *Clostridium bifermentans* by Gas Chromatography", (1970) Canadian Journal of Microbiology 16:1071-1078 Brooks et al.

"Analysis by Gas Chromatography of Hydroxy Acids Produced by Several Species of Neisseria" Canadian *Journal of Microbiology* 18:157-168 (1972) Brooks et al.

"Analysis by Gas Chromatography of Fatty Acids Found in Whole Cultural Extracts of Neisseria Species", *Can. J. Microbiol.* 17:531-541 (1970).

Kostelc et al. "Salivary Volatiles as Indicators of Periodontitis" *J. Periodont* Res. 18: 185-192 (1980).

Matsumota et al., "Identification of Volatile Compounds in Human Urine", J. Chromatogr 85: 31-34 (1973).

Zlatkis et al., "Concentration and Analysis of Volatile

Urinary Metabolites" J. Chromatogr. Sci. 11:299-302 (1973).

"Botulism: A Pyrolysis-gas-liquid Chromatographic Study" J. *Chromatogr. Sci.* 16: 623-629 (1978).

"Quantitative Methods for the Gas Chromatographic Characterization of Acidic Fermentation By-products of Anaerobic Bacteria", by Bohannon et al., J. of Chromatogr. Sci. 16: 28-35 (1978).

"Analysis of Amines and Other Bacterial Products by Head-Space Gas Chromatography" by Larsson et al. Acta Path. Microbiol. Scand. Section B 86: 207-213.

"Methylmercaptan and DMDS Production from Methionine by Proteus Species Detected by Head-Space Gas-Liquid Chromatography" by *Hayward* et al., *J. of Clin. Microbiol.* 6: 187-194 (1977).

"Characteristic Gamma-Lactone Odor Production of the Genus Pityrosporum" by Labows et al. *Appl. and Environ. Micro.* 38: 412-415 (1979).

"The Chemistry of Some Microbially-Induced Flavor Defects in Milk and Dairy Foods", by Morgan, *Biotech. Bioeng.* 18:953-965 (1976).

Liebich et al., "Volatile Substances in Blood Serum: Profile Analysis and Quantitative Determination"J. Chromatogr. 142: 505-516 (1977).

van den Dool et al. "A Generalization of the Retention Index System Including Linear Programed Gas-Liquid Chromatography", *J. of Chromatography*, vol. 11, pp. 463-471 (1963).

Withycombe et al., "Isolation and Identification of Volatile Components from Wild Rice Grain" *J. of Agricultural Food Chemistry*, vol. 6, pp. 816-821 (1978).

Tonzetich, "Direct Gas Chromatographic Analysis of Sulfur Compounds in Mouth Air In Man", *Archives of Oral Biology*, vol. 16 pp. 587-597 (1971).

Budzikiewicz et al. "Mass Spectrometry of Organic Compounds" pp. 129-138, Holden-Day, Inc., San Francisco (1967).

Dwivedi et al. "Carbonyl Production From Lipolyzed Milk Fat by the Continuous Mycelial Culture of Penicillium Roqueforti" *J. Food Science*, 39: 83-137 (1974).

Burger et al., "Ketones From the Pedal Gland of the Bontebok" Z. Naturforsch C: Bioscience 316: (1-2): 21-8.

Albone et al. "Bacteria As a Source of Chemical Signals in Mammals" Reprinted pp. 35-43 in D. MullerSchwarze and M. M. Mozell, Editors, Chemical Signals in Vertebrates, Plenum Press, NY (1977).

Ikeshoji, "Bacterial Production of the Ovipositional Attractants for Mosquitos on Fatty Acid Substrates" Appl. Ent. Zool. 10: 239-242.

John N. Labows, K. J. McGinley, Guy F. Webster, & J. J. Leyden, "Headspace Analysis of Volatile Metabolites of *Pseudomonas aeruginosa* and Related Species by Gas Chromatography-Mass Spectrometry".

Gorbach, S. L., J. W. Mayhew, J. G. Bartlett, H. Thadepalli, and A. B. Onderdonk, 1976, Rapid Diagnosis of Anaerobic Infections by Direct Gas-Liquid Chromatography of Clinical Specimens, J. Clin. Invest 57:478-484.

"Diet and Oral Health" by Dominick P. DePaola, D.D.S., and Michael C. Alfano, D.M.D., Ph.D.; Nutrition Today; May/Jun. 1977.

Berg, M. Burrill, D. Y., and Fosdick, L. S. (1947), Chemical Studies In Periodontal Disease, IV. Putrefaction Rate As Index of Periodontal Diseases, J. Dent, Res. 26: 67-71.

Law, D. B., Berg, M. S., and Fosdick, L. S., (1943) Chemical Studies In Periodontal Disease, J. Dent. Res. 22: 373-379.

Tonzetich, J., Preti, G. and Huggins, G. R., (1978) Changes in Concentrations of Volatile Sulfur Compounds of Mouth Air During the Menstrual Cycle, J. Int. Med., Res. 6: 245-254.

Jellum et al., (1973) J. Anal. Chem. 45 (7) 1099-1106.

Thompson and Markey, J. Anal. Chem. 47 (8): 1313-1321.

Hutterer et al., Clin. Chem. 17 (8): 789-794.

Zlatkis et al., Journal of Chromatographic Science, 11: 299-302 (Jun. 1973).

Preti & Huggins, (1977) "The Human Vagina" Chapter 10, 1978.

Tonzetich, J. 1978 Oral Malodour: An Indicator of Health Status and Oral Cleanliness, Int. Dent. J. 28: 309-319.

Dubowski, Clinical Chemistry 20 (8), 966-972, 1974.

Teranishi et al., Anal. Chem. 44 (1), 18-20, 1972.

Chen et al., J. of Lab. and Clinical Medicine, vol. 75, No. 4, pp. 628-635, 1970 a,b.

Orban, Oral Histology and Embryology, pp. 269-271, 1972.

MacFarlane and Mason, Oral Mucosa In Health, Blackwell Scientific Publications, pp. 113–116, 1975.
Afonsky, University of Alabama Press, pp. 97–104, 1961.
Miles, British Dental Journal 104: 235–248, 1958.
Spouge, The Dental Practioner and Dental Record; vol. XIV (8); 307–318, 1964.
Tonzetich and Kestenbaum, Arch. Oral Biol. 14: 815–827, 1964.
McNamara et al., Oral Surg. 34: 41–48, 1972.
Hardie and Bowden, The Normal Microbial Flora of Man, pp. 47–61, 1974.
Berg and Fosdick, J. Dental Res. vol. 26, pp. 67–71, 1946.
Berg and Fosdick, J. Dental Res. vol. 25, pp. 73–81.
Tonzetich, J. Periodont, 48: 13–20, 1977.
Loe, J. of Periodontology, V. 36 (1): 37/209–45/217, 1965.
Loe and Sillness, Acta Odont. Scand. 21: 533–549, 1963.
Lindhe and Attstrom, J. Periodont. Res. 2: 194–198, 1967.
Lindhe et al., J. Periodont. Res. 3: 12–20, 1968.
Holm-Pedersen and Loe, J. Periodont, Res. 2:13–20, 1967.
Iusem, Oral Med. 3: 1516–1520, 1950.
Main and Richie, Brit. J Dermatology 79: 20–30, 1967.
Dreizen et al., Oral Surgery, Oral Medicine and Oral Pathology, 69: 278–283, 1965.
Berg et al., J. Dental Res. vol. 26, pp. 67–71, 1947.
Rizzo, Periodontics 5: 233–236, 1967.
Tonzetich and Richter, Arch. Oral Biology, 9: 39–45, 1964.
Tonzetich and Lo, Arch. Oral Biology, 23: 875–880, 1976.
Golub et al., J. Periondontal Res. 6: 243–251, 1971.
Tonzetich, J. and Ng, S. K. 1976, Reduction of Malodor by Oral Cleaning Procedures, Oral Surg., Oral Med., Oral Path., 42: 172–181.
Loe, H. and Silness, J. 1963, Periodontal Disease in Pregnancy, I. Prevalance and Severity, Acta Odont. Scand. 21: 533–549.
Sillness, J. and Loe, H. 1964, Periodontal Disease in Pregnancy, II Correlation Between Oral Hygiene and Periodontal Condition, Acta. Odont. Scand., 22: 121–135.
Ramfjord, S. P. 1959, Indices for Prevalance and Incidence of Periodontal Disease J. Perio. 30: 51–59.
The Periodontal Index (Russell, A. L. 1956, A System of Classification and Scoring for Prevalence Surveys of Periodontal Disease, J. Dent. Res. 35: 350–359).
Jamison, J. 1960 Prevalence and Severity of Periodontal Disease on a Sample Population Thesis Abstract, University of Michigan, School of Public Health, Ann Arbor.
Van denDool, H. and Kratz, P. D. 1963, A Generalization of the Retention Index System Including Linear Temperature Programmed Gas-Lipid Partition Chromatography, J. Chromatog., 11: 463–471.
Watson, J. T. and Biemann, K. 1965, Direct Recording of High Resolution Mass Spectra of Gas Chromatographic Effluents, Anal. Chem. 37: 844–851.
Tonzetich, J. 1971, Direct Gas Chromatographic Analysis of Sulphur Compounds in Mouth Air in Man. Archs. Oral Biol. 16(4): 587–597.
Rao, G. S., McLennon, D. A., Hefferren, J. J., Appelgren, R. and Robinson, P. J. 1978, Gas Chromatographic Analysis of Mouth Odor as a Potential Diagnostic Aid in Periodontal Disease, J. Dent. Res. 57(A):244; IADR Abstracts 1978, Abstract 680.
J. G. Kostelc et al., J. Dent. Res., vol. 58, Jan. 1979, p. 174, (IADR Abstracts, 1979) Abstract No. 325.
K. D. Brunnemann et al., Chem. Abstracts, vol. 89, 1978, 89: 194115x.

*Primary Examiner*—Sidney Marantz
*Attorney, Agent, or Firm*—Woodcock, Washburn, Kurtz, Mackiewicz & Norris

[57] ABSTRACT

Method for precisely ascertaining the time of ovulation by monitoring the concentration of alcohols in the range of $C_{10}$–$C_{16}$, particularly dodecanol. A spike in the concentration of such compound(s) is indicative of time of ovulation.

8 Claims, 4 Drawing Figures

METHOD DETECTING OVULATION BY MONITORING DODECANOL CONCENTRATION IN SALIVA

RELATED PATENTS AND PATENT APPLICATIONS

The present application is related to U.S. Pat. Nos. 3,986,494, 4,010,738; and 4,119,089.

The present application is also related to copending patent application Ser. No. 35,018 filed May 1, 1979, U.S. Pat. No. 4,334,540, entitled "Method of Diagnosing Periodontal Disease Through The Detection of Pyridine Compounds"; and to co-pending patent application Ser. No. 929,162, filed July 28, 1978, now abandoned, entitled "Method of Predicting and Determining Ovulation By Monitoring the Concentration of Volatile Sulfur-Containing Compounds Present in Mouth Air".

Each of these above identified patents and patent applications are hereby incorporated by reference as if fully set forth herein.

BACKGROUND OF THE INVENTION

The present invention relates to the field of detection and diagnosis of ovulation in female mammals through the detection of secondary characteristics occurring during or at the time of ovulation, and more particularly to the identification of and detection of secondary characteristics as they appear in human females.

There has for many years been a need to detect and diagnose the precise time of ovulation in a given female mammal. It can be of great importance, for example, to pinpoint the time of ovulation to insure that fertilization occurs. Alternatively, it may be important for other medical reasons to diagnose ovulation.

Economically, it is of great interest to livestock breeders, particularly cattle breeders, to be able to detect the times of ovulation of cows in the herd in order to insure that offspring production is maximized. In dairy herds, for example, conventional techniques for determining ovulation result in as many as 50% of the ovulatory cycles of a given cow being undetected by the breeder. Since artificial insemination is now almost exclusively used to produce fertilization, auxillary means capable of detecting each incidence of ovulation is in great demand.

Other than those tests suggested in the above mentioned related patents and patent applications, there are no simple, inexpensive tests by which a doctor, breeder or other individual may diagnose the occurrence of ovulation. Since the occurrence of subsequent vaginal bleeding may not be a reliable indicator that ovulation has indeed occurred, and since, in many instances, it would be desirable to begin treatment for suspected condition without awaiting the onset of menstruation to determine that ovulation has, in fact, occurred, a need exists for a method to accurately diagnose the occurrence of ovulation at the time of its occurrence during a menstrual cycle.

The occurrence of ovulation can be established with some certainty through various prior art methods. For a review of the surgical, clinical and biochemical or histological techniques heretofore suggested to diagnose ovulation and to predict the onset of the fertile period, please refer to the descriptions appearing in the above mentioned related patents and patent applications, and particularly to columns 1–5 of U.S. Pat. No. 4,119,089.

Although the above mentioned patents and patent applications have added to the armamentarium of methods for diagnosing the occurrence of ovulation, a need nonethless exists to develop other methods and techniques which may be used alone or in combination with existing methods to pinpoint the time of mammalian ovulation.

SUMMARY OF THE INVENTION

The present invention is predicated upon the finding that certain long chain alcohols, such as dodecanol, exhibit a unique cyclical behavior during the course of a female's menstrual cycle, and accordingly, may be utilized to provide a novel method of diagnosing ovulation. By monitoring the concentration of such alcohols, particularly dodecanol, during the menstrual cycle beginning after menses, and by providing an indicator means for qualitatively and quantitatively responding to the concentration of such alcohol(s), a method is provided wherein significant increases in the concentration of such alcohol(s) is diagnostic of ovulation.

Generally, the method of the present invention comprises the monitoring of saliva for the concentration of certain long-chain alcohols, particularly those having 10–14 carbon atoms, and more particularly dodecanol, by providing an indicator means for qualitatively and quantitatively responding to concentration of said alcohol compounds in saliva, whereby the means for indicating that concentration diagnosis the precise time of ovulation.

The present invention provides a simple, reliable method of detecting ovulation by detecting a single "peak" or "spike" of such alcohol which occurs at the time of ovulation. The alcohol, particularly dodecanol, content of saliva, as detected in the headspace of an incubated sample thereof, is believed to be a secondary characteristic which is responsive to elevated levels of female sex hormones. Unlike other such salivary compounds, dodecanol remains at a relatively constant base level throughout the menstrual cycle, exhibiting a single peak or spike precisely corresponding to ovulation. Unfortunately, the biochemical mechanisms and pathways leading to the production of elevated amounts of dodecanol precisely at the time of ovulation are not currently understood. Nonethless, the unique correspondence of such dodecanol spikes to the time of ovulation, and only to the time of ovulation, is of particular use to the diagnostic clinician.

Accordingly, the primary object of the present invention is the provision of a simple, safe, reliable method of diagnosing ovulation by monitoring the concentration of certain long-chain alcohols in saliva over the course of a given menstrual cycle, a marked increase in the concentration of such long-chain alcohols, and particularly dodecanol, being diagnostic of ovulation.

A further object of the present invention is elimination of extensive histological or biochemical tests which might otherwise be used to determine the occurrence of ovulation.

These and other objects of the present invention will become apparent from the following more detailed description.

DESCRIPTION OF THE PREFERRED EMBODIMENTS

Unless otherwise indicated herein, the methods and procedures utilized in conducting the following examples are those described in the aforementioned related United States Patents and patent applications, and particularly U.S. Pat. No. 4,119,089, which have been incorporated by reference as if fully set forth herein.

Figure 1:
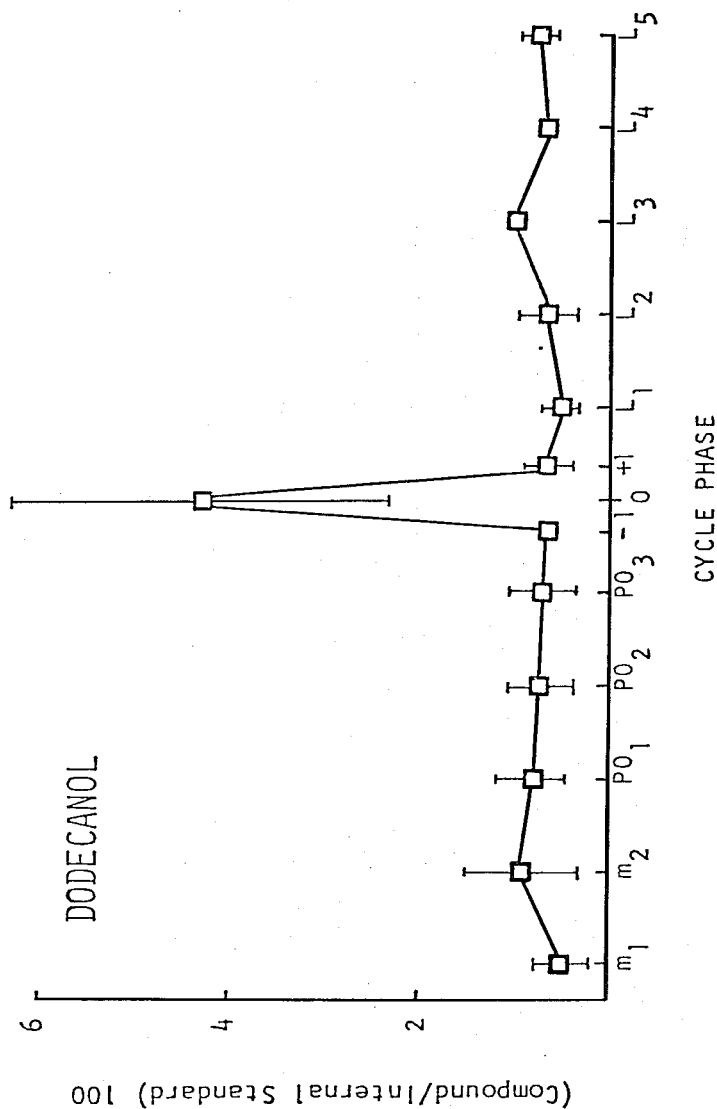
FIG. 1 is a graph of concentration changes for dodecanol in salivary head space after 90 minutes of incubation at 37° C. which was compiled from data collected from four cycles of two human females, a four fold increase in the concentration of dodecanol being indicated at the time of ovulation (cycle phase 0)

FIG. 1 is a graph compiled from data for two cycling females, each over two menstrual cycles. Each of these females donated basal morning saliva each day during such cycles. Basal body temperature charting was employed to ascertain, to the degree possible, the day of ovulation. Although one cycle showed an abnormally large follicular phase and short luteal phase, isolated blood samples obtained in the short luteal phase showed progesterone values indicative of ovulation. FIG. 1 shows the combined data for these four cycles presented using the method of Doty (1979). This method enables menstrual cycles of variable lengths to be combined and is based on the initial normalization of new matrix data to eliminate extraneous between-cycle variability, followed by the assignment of the normalized data to sets of discrete cycle phases using a weighted-average technique.

Figure 2:
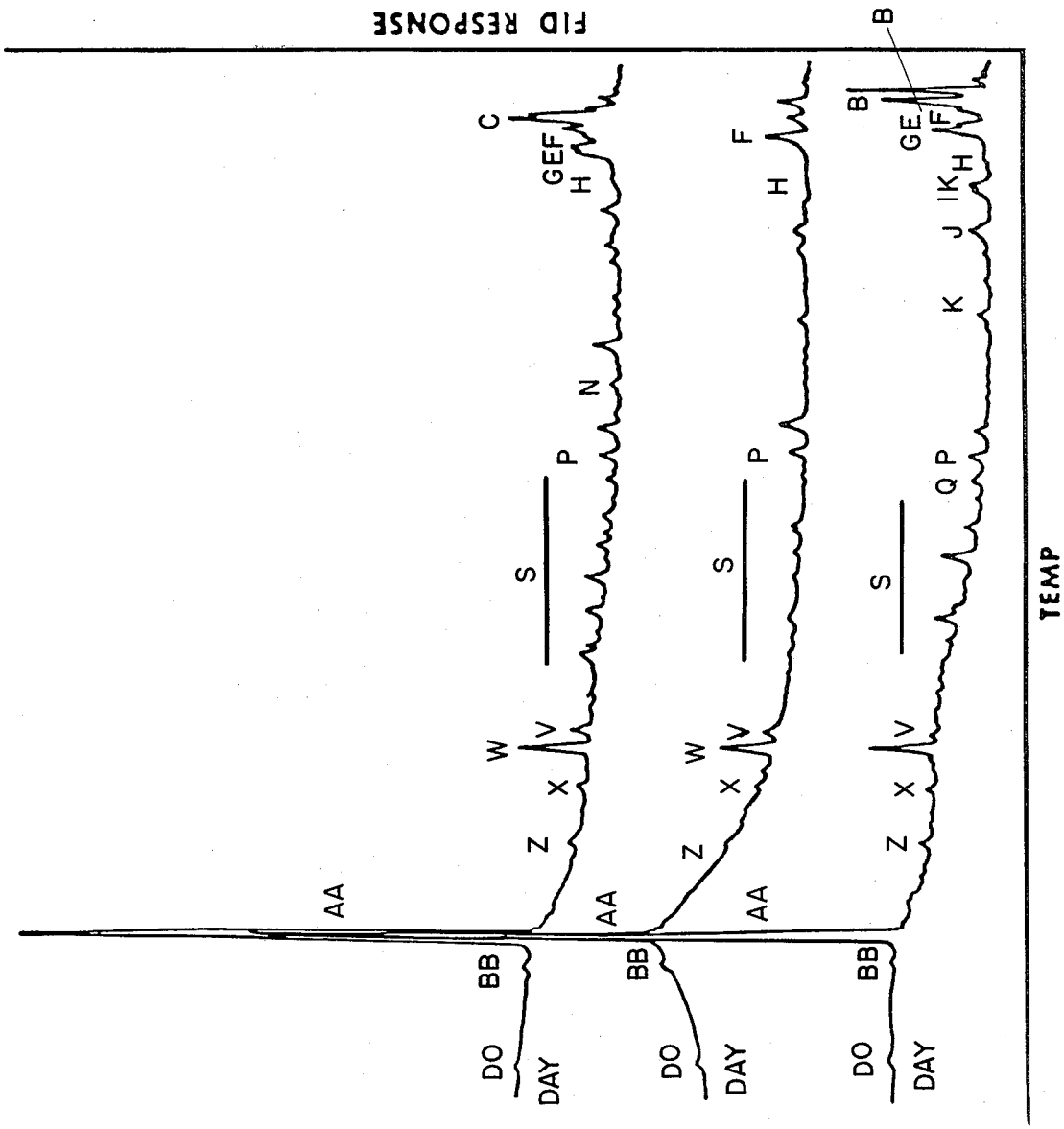
FIG. 2 is a gas chromatographic profile showing the relative gas chromatographic retention times for which mass spectral fragmentation patterns have been matched with known compilations of mass spectra to indicate the relative concentrations of compounds identified in the salivary head space of a single subject at days 3, 12 and 26 of her menstrual cycle.

Gas chromatography profiles and GC/MS data were obtained on salivary volatiles obtained from the aforementioned saliva samples. For purposes of comparison, such samples were also compared to samples provided by male donors. In FIG. 2, a typical gas chromatographic profile is set forth wherein the relative gas chromatographic retention times of salivary head space compounds are provided for a representative female. In the profile set forth, the mass spectral fragmentation patterns have been matched with known compilations of mass spectra (MIT-Mass Spectrometry Laboratory). This data, when compared to data collected for representative males, tends to indicate that healthy male and female subjects produce many of the same salivary constituents. Female samples were found to possess 6-7 compounds, appearing to be sesquiterpenes having a molecular weight of 204 and a probable elemental composition of $C_{15}H_{24}$ (in the areas bracketed by "S" in FIG. 2) which were not found in samples taken from male subjects. It is believed that beta-caryophylene and cedrene are among these compounds present in cycling females.

One of the subject females showed the presence of alkyl isothiocyanate in her samples while none of this compound was found to exist in any of the cycling females which had been examined in connection with studies conducted in our laboratory. This compound was apparently the result of the subject's diet which included an almost daily intake of gourmet mustard containing mustard seeds. Alkyl isothiocyanate is a constituent of mustard seeds (Fernelli's Handbook of Flavor Ingredients, 1975; Merke Index, 1976). As set forth in Table One, hereinafter, numerous compounds have been found to consistently appear in salivary samples from both female and male subjects, and are easily identified by their relative retention times and mass spectra. It should be noted, however, that with present instrumental facilities and manpower, it took approximately one year to run the gas chromatograms, manually interpret the mass spectra and quantitate the desired constituents for presentation here.

TABLE ONE

SALIVARY VOLATILES EXAMINED FOR CHANGES ACROSS A MENSTRUAL CYCLE

| | MOLECULAR WT. | CYCLICAL CHANGES INDICATED[2] |
|---|---|---|
| ACETONE | 58 | |
| ETHANOL | 46 | |
| PROPANOL | 60 | |
| DIMETHYLDISULFIDE | 94 | * |
| DIMETHYLTRISULFIDE | 126 | * |
| DODECANOL | 186 | * |
| PHENOL | 94 | |
| p-CRESOL | 108 | |
| TETRADECANOL | 214 | |
| INDOLE | 117 | * |
| SKATOLE | 131 | |
| DIPHENYLAMINE | 169 | * |

[1]Listed with respect to increasing retention time
[2]See below for discussion

While there is considerable individual variation in the data obtained as to each of the above identified compounds at given points in the menstrual cycle of the subjects, various characteristics are apparent, particularly for those compounds noted as indicating cyclical changes. The results obtained for dimethyldisulfide and dimethyltrisulfide are consistent with the results reported in U.S. Pat. No. 4,119,089. In general, the concentration changes for the above identified compounds range from between 2-10 fold when going from day when concentrations are low to days when concentrations are high. Such variations in concentration are graphically set forth in FIG. 2, showing relative concentrations of the various compounds at given points in the menstrual cycle. In FIG. 2, the Y axis shows the concentration (in micrograms) of each compound relative to the amount of internal standard recovered times 100. Because of the relatively small number of cycles, considerable deviation was seen for many of the data points. In Table Two, set forth below, the codes for the various compounds set forth in FIG. 2 are provided, from which the identity of each of the subject compounds may be ascertained:

TABLE TWO

| COMPOUNDS | CODE |
|---|---|
| ETHANOL | C |
| PROPANOL | E |
| BUTANOL | I |
| PENTANOL | L |
| DODECANOL | V |
| TETRADECANOL | Z |
| 2-ETHYLHEXANOL | P |
| PHENOL | W |
| p-CRESOL | X |
| DIETHYL PHTHALATE (STD) | AA |
| DIMETHYL DISULFIDE | H |
| DIMETHYL TRISULFIDE | N |
| DIMETHYL SULFONE | U |

TABLE TWO-continued

| COMPOUNDS | CODE |
| --- | --- |
| ALKYL ISOTHIOCYANATE | M |
| INDOLE | BB |
| SKATOLE | CC |
| DIPHENYL AMINE | DD |
| 2-PIPERIDONE | Y |
| TRIMETHYL AMINE | A |
| BENZENE | D |
| TOLUENE | G |
| $C_7$-$C_{12}$ ALKANES | B |
| $C_{17}$-$C_{22}$ ALKANES | T |
| $C_2$-$C_4$ ALKYL BENZENES | K |
| STYRENE | J |
| NAPHTHALENE | R |
| BENZALDEHYDE | B |
| TETRACHLOROETHYLENE | F |
| $C_2$-$C_6$ ACIDS | O |
| SERIES OF SEQUITERPENES | S |

The concentration change for dodecanol, as indicated in FIG. 1, was remarkable in light of the fact that a sharp 4-fold change in concentration of this compound occurred precisely at the time of ovulation was indicated. Unlike the other compounds examined in a quantitative manner, this sharp increase at mid-cycle is the only elevation in concentration which was observed for dodecanol. Accordingly, this compound is presently the preferred compound for monitoring in accordance with the method of the present invention, and should provide a reliable diagnostic indicator of ovulation.

Figure 3:
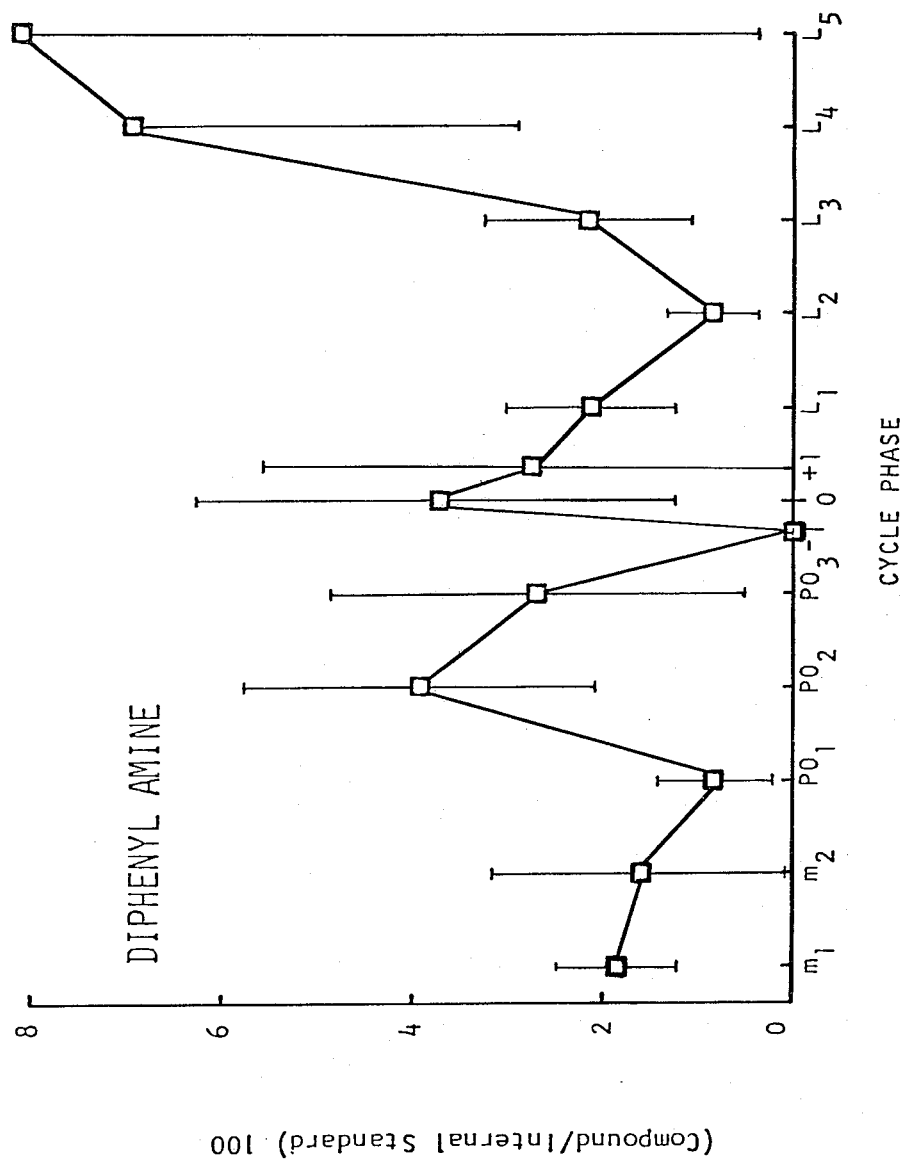
FIG. 3 is a graph similar to FIG. 1 but showing concentration changes of diphenyl amine.
Figure 4:
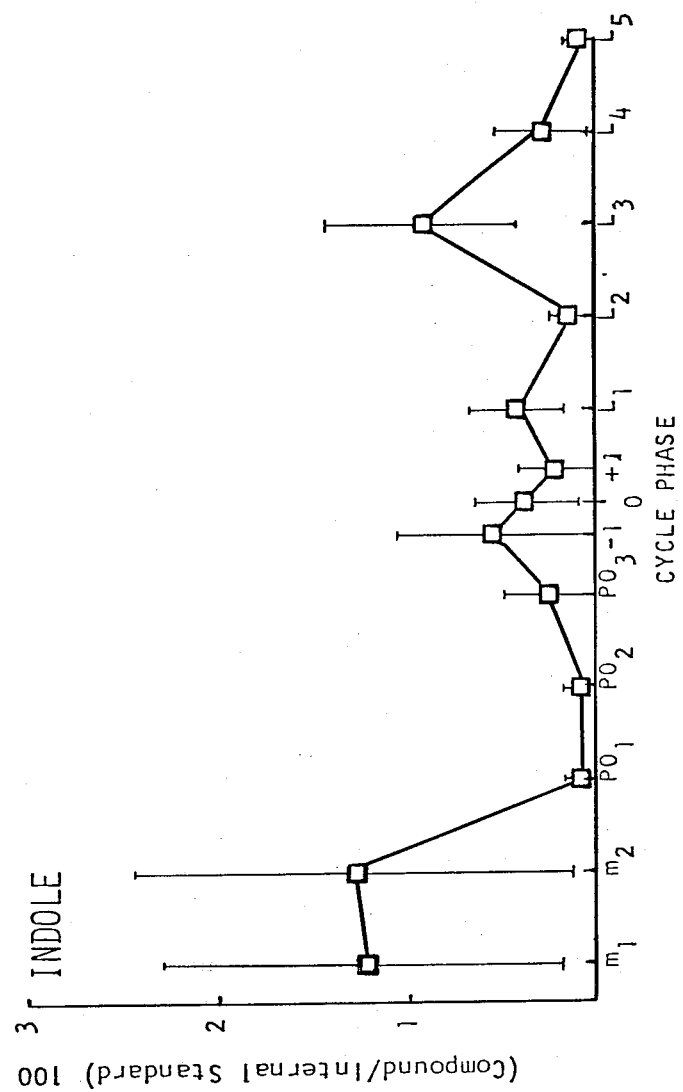
FIG. 4 is a graph similar to FIGS. 1 and 3 but showing concentration changes of indole.

For purposes of comparision, the cyclical changes for diphenyl amine and indole are set forth in FIGS. 3 and 4. It will be noted that relatively high concentrations of diphenylamine have been found at preovulatory phase $PO_2$, that sharp drops in that concentration have been found at the day prior to ovulation, and that concentrations returned to higher levels at the time of ovulation. Concentration variations for indole over the period of one menstrual cycle, are similarly clearly cycle dependent. Such compounds may be used in combinations with other indicators, to confirm the particular menstrual phase of a given subject.

It is currently believed that the metabolic pathways which lead to the detection of a large dodecanol spike at the time of ovulation are also likely to cause the spiking of other relatively long-chain alcohols having in the range of 10–16 carbon atoms, particulary 11–14 carbon atoms.

The data presented for dodecanol is, however, unique, and may prove to be superior even to the detection of other compounds which are known to cycle, such as various volatile sulphur compounds, in that a sharp spike in the concentration of such compounds was detected for every subject at the time of ovulation, and is believed to occur only once during the entire menstrual cycle. Accordingly, and extremely reliable method of diagnosing ovulation in a cycling female mammal is disclosed wherein the concentration of dodecanol is monitored during said menstrual cycle to identify the occurrance of said spike, whereupon a relative transitory yet quite significant increase in the concentration of such compound is diagnostic of ovulation.

We claim:

1. A method of diagnosing ovulation in female mammals comprising the steps of:
   (a) monitoring the saliva of one of said mammals during the fertility cycle for a dodecanol occurring in the saliva of said mammals; and
   (b) providing an indicator means for qualitatively and quantitatively responding to variations in the concentration of said dodecanol in said saliva; whereby said means for indicating said variations in concentration diagnosis ovulation in said female mammal.

2. The method of claim 1 wherein said female mammal is a human female.

3. The method of claim 1 wherein said indicator is a gas chromograph-mass spectrometer.

4. The method of claim 1 wherein said method comprises the steps of incubating said saliva for a preselected period of time and monitoring the concentration of said dodecanol in said saliva.

5. The method of claim 4 wherein said preselected period of time is from between about 30 to 120 minutes at about 37° C.

6. The method of claim 1 wherein said indicator means responds to increases in the concentration of said dodecanol.

7. The method of claim 6 wherein said increases of concentration of said dodecanol represent at least a doubling of the concentration of said dodecanol in said saliva.

8. The method of claim 7 wherein said increases in dodecanol represent an increase of about four times the concentration of said dodecanol in said saliva.

* * * * *